US00PP12483P2

(12) United States Plant Patent
Bartels et al.

(10) Patent No.: US PP12,483 P2
(45) Date of Patent: Mar. 26, 2002

(54) ROSE PLANT NAMED 'BAPOLLU'

(75) Inventors: Gosen B. H. Bartels, Aalsmeer; Peter Adriaan van der Pol, Overberg; Herman Masselink, Wageningen, all of (NL)

(73) Assignee: Bartels Breeding, B.V., Aalsmeer (NL)

( * ) Notice: Subject to any disclaimer, the term of this patent is extended or adjusted under 35 U.S.C. 154(b) by 0 days.

(21) Appl. No.: 09/336,571

(22) Filed: Jun. 21, 1999

(51) Int. Cl.[7] ..... A01H 5/00
(52) U.S. Cl. ..... Plt./103
(58) Field of Search ..... Plt./101, 102, 103, Plt./104

(56) References Cited

PUBLICATIONS

UPOV–ROM, 2001/01, Plant Variety Database, GTI Jouve Retrieval Software, citation for 'Bapollu'.*
Copy of NL PBR R002547 and copy of Proposal for Varietal Denomination for 'Bapollu'.*

* cited by examiner

*Primary Examiner*—Howard J. Locker
(74) *Attorney, Agent, or Firm*—C. A. Whealy

(57) ABSTRACT

A distinct cultivar of Rose plant named 'Bapollu', characterized by its upright stems with rounded to pyramidal display of dark red hips; thornless stems; very long post-production longevity, cut stems with hips typically last at least 90 days; and resistance to Powdery Mildew.

2 Drawing Sheets

BACKGROUND OF THE INVENTION

The present invention relates to a new and distinct cultivar of Rose plant, botanically known as *Rosa hybrida*, commercially used as a cut rambler Rose stem with hips, and hereinafter referred to by the cultivar name Bapollu.

The new cultivar is a product of a planned breeding program conducted by the Inventors in Wageningen, The Netherlands. The objective of the breeding program was to develop thornless cut Rose selections with dark red hips and resistance to Powdery Mildew.

The new cultivar originated from a cross made by the Inventors of two unidentified proprietary seedling selections. The cultivar Bapollu was discovered and selected by the Inventors as a plant within the progeny of the stated cross in a controlled environment in Wageningen, The Netherlands, in 1993.

Compared to plants of the female parent seedling selection, plants of the new Rose have brighter red-colored hips and are thornless. Compared to plants of the male parent seedling selection, plants of the new Rose are more resistant to Powdery Mildew.

Asexual propagation of the new cultivar by cuttings taken at Wageningen, The Netherlands, has shown that the unique features of this new Rose plant are stable and reproduced true to type in successive generations.

SUMMARY OF THE INVENTION

The following traits have been repeatedly observed and are determined to be the unique characteristics of 'Bapollu'. These characteristics in combination distinguish the new Rose plant as a new and distinct cultivar:

1. Upright stems with rounded to pyramidal display of dark red hips.

2. Thornless stems.

3. Very long postproduction longevity; cut stems with hips typically last at least 90 days.

4. Resistant to Powdery Mildew.

Compared to plants of the commercial Rose cultivar Kolsens, not patented, plants of the new Rose have brighter red-colored hips. In addition, plants of the cultivar Kolsens flower after about one year of growth whereas plants of the new Rose flower after about two years of growth.

The new Rose plant has not been observed under all possible environmental conditions. The phenotype may vary significantly with variations in environment such as temperature, light or fertility level, without, however, any variance in genotype.

BRIEF DESCRIPTION OF PHOTOGRAPHS

The accompanying colored photographs illustrate the new Rose plant, showing the colors as true as it is reasonably possible to obtain in colored reproductions of this type. Colors in the photographs may differ slightly from the color values cited in the detailed botanical description which accurately describe the actual colors of the new Rose. The photograph on the first sheet comprises a side perspective view of typical cut stems of the new Rose plant. The photograph on the second sheet comprises a close up view of typical flowers of the new Rose plant.

DETAILED BOTANICAL DESCRIPTION

The following observations, measurements and values describe plants grown in Wageningen, The Netherlands, in open field conditions which closely approximate commercial production conditions.

In the following description, color references are made to The Royal Horticultural Society Colour Chart except where general terms of ordinary dictionary significance are used.

Classification:
*Botanical.*—*Rosa hybrida* cultivar Bapollu.
*Commercial.*—Cut Rose stem with dark red hips.
Parentage:
*Male or pollen parent.*—Unidentified *Rosa hybrida* proprietary seedling selection.

*Female or seed parent.*—Unidentified *Rosa hybrida* proprietary seedling selection.

Propagation:

*Type.*—Cuttings.

*Time to initiate roots.*—Summer: About 28 days at 25° C. Winter: About 42 days at 18° C.

*Rooting habit.*—Fine, fibrous and well-branched.

Plant description:

*Form.*—Upright; pyramidal; rambling.

*Vigor.*—Vigorous.

*Growth rate.*—Rapid.

*Plant height.*—About 2 meters.

*Plant width.*—About 3 meters.

*Flowering stems.*—Length: About 60 cm. Diameter: About 1 cm. Weight: About 100 grams per lateral stem without leaves. Strength: Very strong. Quantity of lateral branches: Freely branching; typically about ten per plant. Texture: Smooth, no thorns or prickles. Main stems may have a few thorns. Color: Green, 143C.

*Foliage description.*—Leaves arranged alternately, compound with five or seven leaflets per leaf, and generally symmetrical. About 50 compound leaves per lateral branch. Leaf length: About 10 cm. Leaf width: About 4 cm. Terminal leaflet length: About 2.5 cm. Terminal leaflet width: About 2 cm. Shape: Ovate. Margin: Serrate. Texture: Glabrous. Color: Young foliage, upper surface: 137A. Young foliage, lower surface: 137C. Mature foliage, upper surface: 137A. Mature foliage, lower surface: 137C. Petiole and stipules: Close to 137A.

Flower description:

*Flower type and habit.*—Typical single Rosa-type flowers. Consistently symmetrical rounded flowers. Flowers arranged in panicles. Overall shape of spray formation is rounded to pyramidal. Freely and continuous flowering. Flowers persistent. Typically about 50 flowers per stem.

*Time to flower.*—Plants are usually two-years old prior to flowering.

*Fragrance.*—Intense sweet fragrance.

*Flower diameter.*—About 1.5 cm.

*Flower depth* (*height*).—About 1 cm.

*Flower longevity on plant.*—About 4 days.

*Petals.*—Quantity: Five per flower. Length: About 1 cm. Width: About 1 cm. Shape: Triangular. Color: Upper and lower surfaces, when opening: 158D. Upper and lower surfaces, fully opened: 158D.

*Sepals.*—Quantity: Five per flower. Color: Close to 137A.

*Reproductive organs.*—Many yellow-colored stamens and anthers.

*Pedicels.*—Strength: Strong. Aspect: About 45° to stem. Length: About 1.5 cm. Diameter: About 1 mm. Texture: Smooth. Color: 143C.

*Fruit* (*hips*).—Quantity per stem: About 50. Length: About 1 cm. Width: About 5 mm. Shape: Rounded. Texture: Smooth. Color: Dark red, 42A. Days to ripening: About 80. Postproduction longevity as a cut stem: More than 90 days.

*Seed.*—Length: About 5 mm. Diameter: About 5 mm. Color: Light yellow.

Disease resistance: Resistance to Powdery Mildew has been observed under commercial production conditions.

It is claimed:

1. A new and distinct Rose plant named 'Bapollu', as illustrated and described.

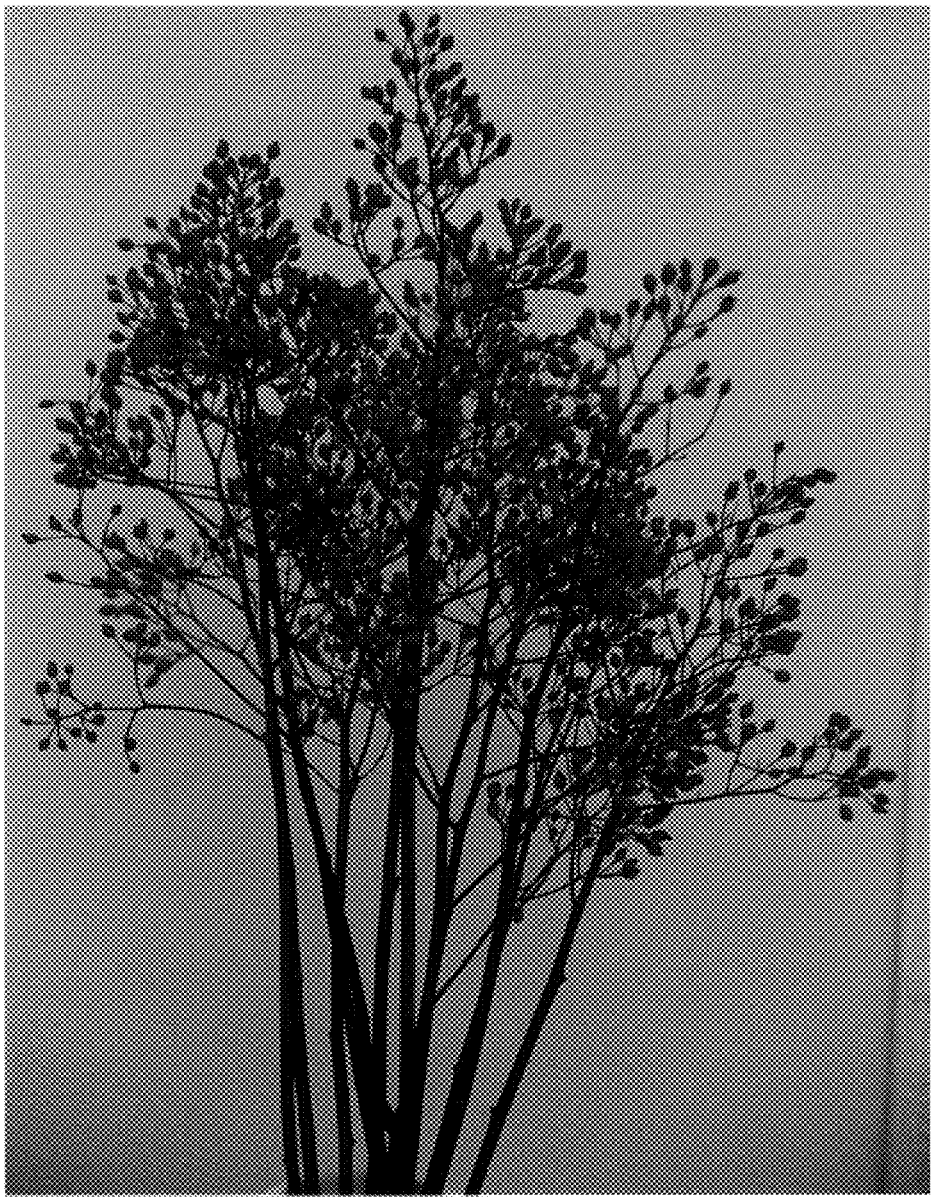

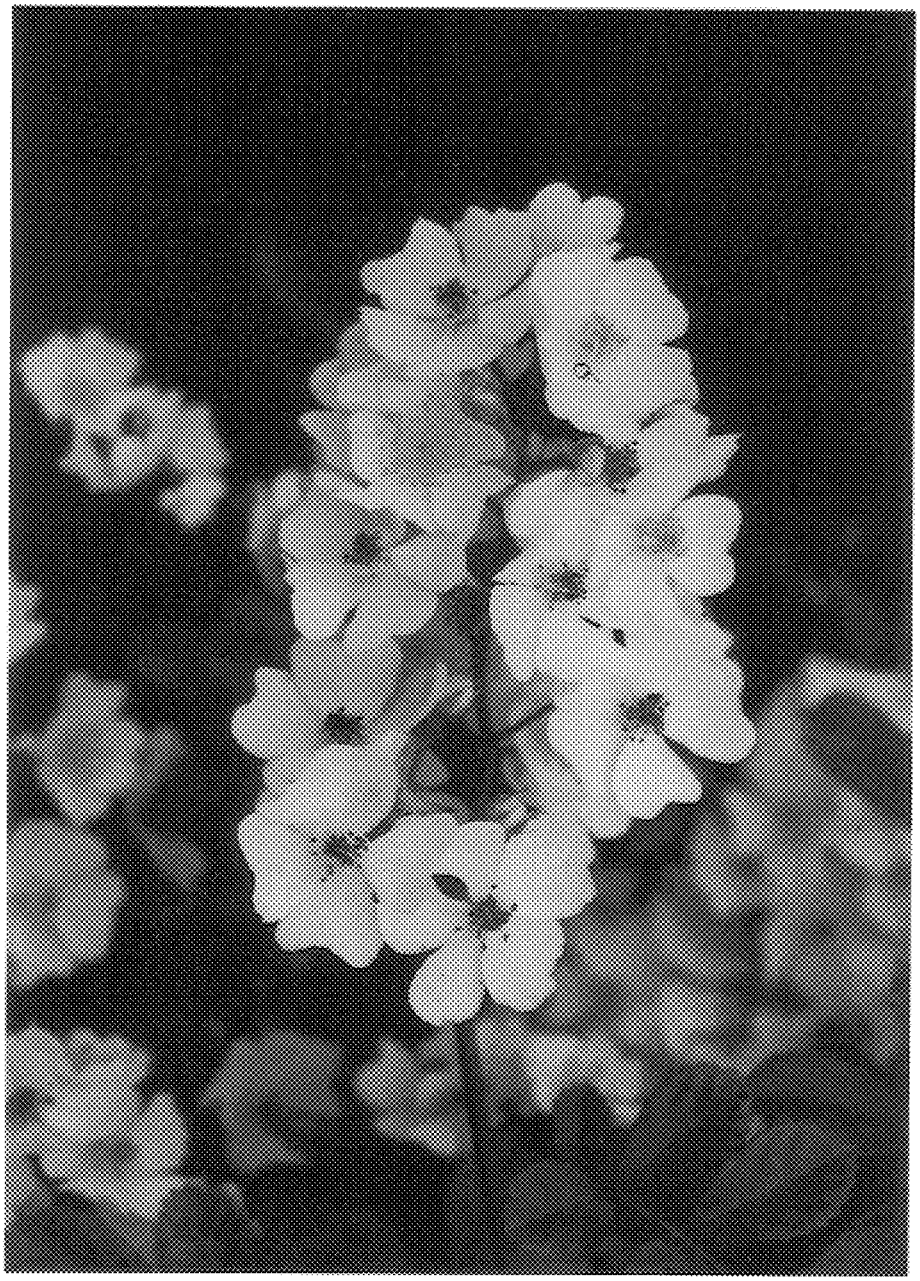

* * * * *